United States Patent
Baarman

(10) Patent No.: US 11,931,474 B2
(45) Date of Patent: Mar. 19, 2024

(54) MOBILE DEVICE DISINFECTION

(71) Applicant: UV Partners, Inc., Grand Haven, MI (US)

(72) Inventor: David W Baarman, Fennville, MI (US)

(73) Assignee: UV Partners, Inc., Grand Haven, MI (US)

( * ) Notice: Subject to any disclaimer, the term of this patent is extended or adjusted under 35 U.S.C. 154(b) by 195 days.

(21) Appl. No.: 17/379,415

(22) Filed: Jul. 19, 2021

(65) Prior Publication Data

US 2021/0346548 A1 Nov. 11, 2021

Related U.S. Application Data

(63) Continuation of application No. 17/251,584, filed as application No. PCT/US2019/036298 on Jun. 10, 2019, now Pat. No. 11,097,026.

(60) Provisional application No. 62/683,933, filed on Jun. 12, 2018.

(51) Int. Cl.
| | |
|---|---|
| A61L 2/10 | (2006.01) |
| A61L 2/26 | (2006.01) |
| H02J 7/00 | (2006.01) |
| H04M 1/17 | (2006.01) |

(52) U.S. Cl.
CPC ............. *A61L 2/10* (2013.01); *A61L 2/26* (2013.01); *H02J 7/0042* (2013.01); *H04M 1/17* (2013.01); *A61L 2202/11* (2013.01); *A61L 2202/14* (2013.01)

(58) Field of Classification Search
CPC ... H04M 1/17; H04M 1/18; A61L 2/10; A61L 2/26; A61L 2202/11; A61L 2202/14; A61L 2/24; H02J 7/0042; H02J 7/0044; H02J 7/0047

See application file for complete search history.

(56) References Cited

U.S. PATENT DOCUMENTS

| | | | |
|---|---|---|---|
| 7,372,044 B2 | 5/2008 | Ross | |
| 8,203,124 B2 | 6/2012 | Havens et al. | |
| 8,431,910 B1 | 4/2013 | Perry | |
| 8,481,970 B2 | 7/2013 | Cooper et al. | |
| 8,964,405 B2 | 2/2015 | La Porte et al. | |
| 9,006,680 B2 | 4/2015 | Bettles et al. | |
| 9,066,987 B2 | 6/2015 | Bettles et al. | |
| 9,138,499 B2 | 9/2015 | Bettles et al. | |

(Continued)

FOREIGN PATENT DOCUMENTS

| | | |
|---|---|---|
| CN | 102078629 | 6/2011 |
| CN | 103618812 | 3/2014 |

(Continued)

OTHER PUBLICATIONS

International Search Report and the Written Opinion of the International Searching Authority for International Application No. PCT/US2019/036298 dated Oct. 4, 2019.

*Primary Examiner* — Tuan D Nguyen

(74) *Attorney, Agent, or Firm* — Warner Norcross + Judd LLP

(57) ABSTRACT

A disinfectant transmissive material incorporated into a case for a mobile device or a supporting surface of a disinfecting charger to enable disinfection of hard to reach areas. The case can be self-disinfecting. The disinfecting charger can have monitoring and safety systems that detect proximity and provide user feedback on safety, disinfection, and charge status along with automatic interlocks to protect the user from overexposure to disinfectant.

20 Claims, 9 Drawing Sheets

(56) References Cited

U.S. PATENT DOCUMENTS

| | | |
|---|---|---|
| 2008/0265179 A1 | 10/2008 | Havens et al. |
| 2010/0004582 A1 | 1/2010 | Bragagna et al. |
| 2010/0044582 A1 | 2/2010 | Cooper et al. |
| 2013/0063922 A1 | 3/2013 | La Porte et al. |
| 2014/0332417 A1 | 11/2014 | Wicks et al. |
| 2015/0115173 A1 | 4/2015 | Kim |
| 2015/0258229 A1 | 9/2015 | Ha et al. |
| 2016/0000953 A1 | 1/2016 | Bettles et al. |
| 2016/0036952 A1 | 2/2016 | Kim et al. |
| 2016/0045633 A1 | 2/2016 | Pagan et al. |
| 2017/0373516 A1 | 12/2017 | Kim et al. |

FOREIGN PATENT DOCUMENTS

| | | |
|---|---|---|
| EP | 3 043 244 | 7/2016 |
| FR | 3 054 942 | 2/2018 |
| JP | 1997-000608 | 1/1997 |
| JP | 3174232 | 6/2001 |
| JP | 3197750 | 8/2001 |
| JP | 2006-180357 | 7/2006 |
| JP | 2012-190574 | 10/2012 |
| JP | 2013-236414 | 11/2013 |
| JP | 2014-068484 | 4/2014 |
| JP | 2017-093938 | 6/2017 |
| JP | 3194014 | 7/2021 |
| KR | 2017-0107801 | 9/2017 |
| WO | 2017/062466 | 4/2017 |
| WO | 2016-186168 | 3/2018 |

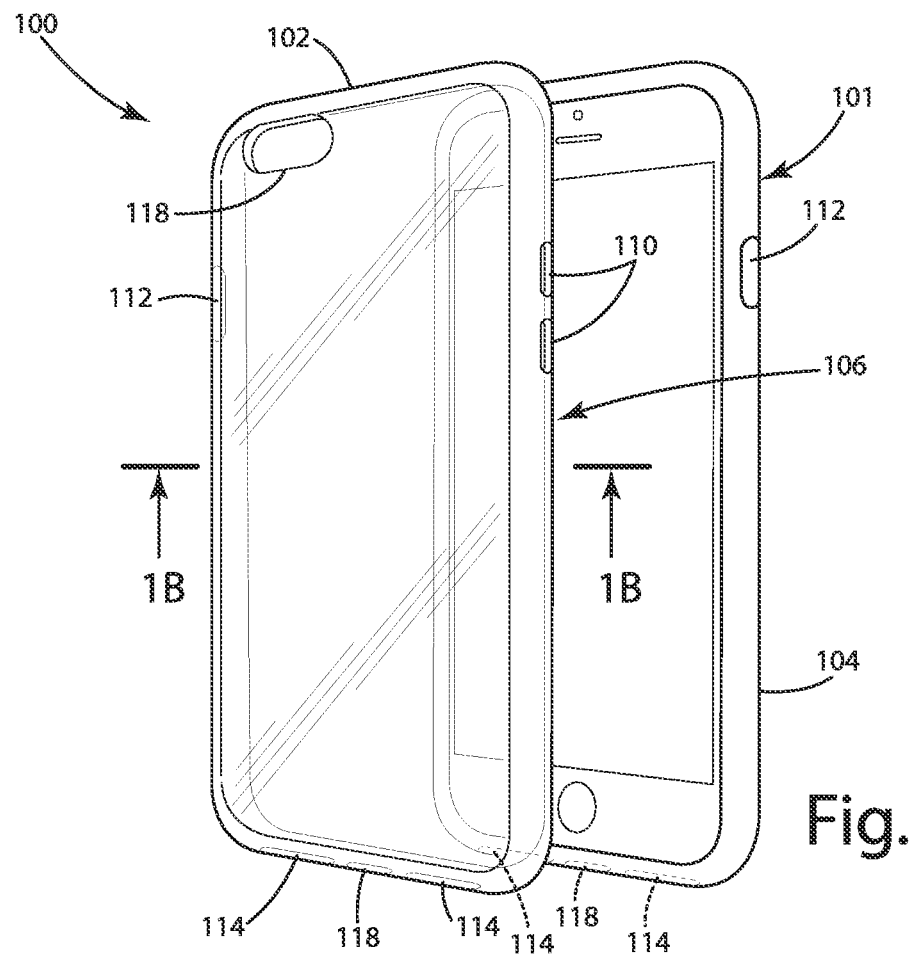
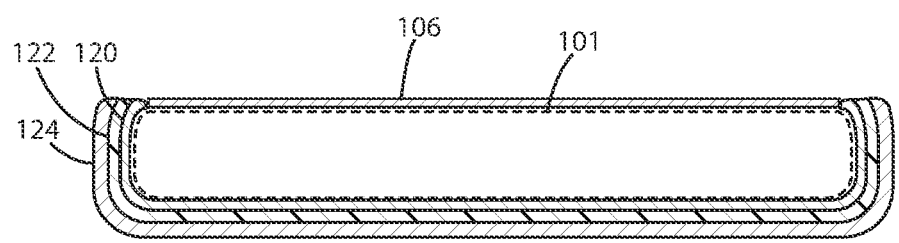
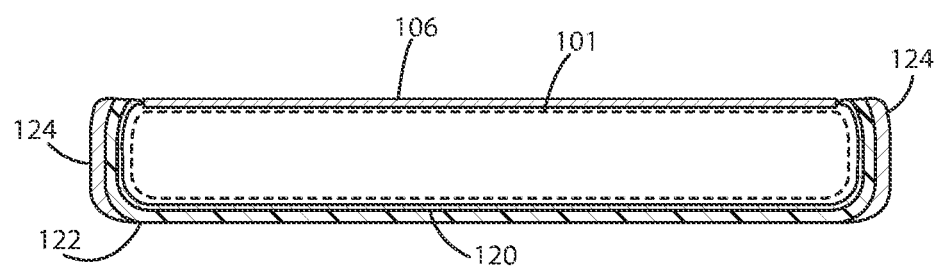

MOBILE DEVICE DISINFECTION

BACKGROUND OF THE INVENTION

The present invention relates to disinfection, and more particularly to systems and methods associated with disinfection.

It is well known that germs can reside on the surfaces of mobile devices and can be transmitted to and from a mobile device through physical contact, resulting in the spread of infection. A variety of efforts have been made to reduce the risks presented by germs and associated infections. For example, there is increasing interest in performing germicidal activities with respect to mobile devices as their use becomes more pervasive in society with the goal of reducing the spread of infection. This includes the growing use of UV ("ultraviolet") disinfection systems to perform repeated or systematic disinfection. There are currently a number of different types of UV disinfection products available on the commercial market. Many conventional UV disinfection products suffer from a variety of shortcomings. For example, UV energy has a tendency to degrade plastics and other materials. As a result, conventional UV disinfection treatment regimens may have the unintended consequence of causing excessive undesirable damage to objects in and around the treatment ranges.

Some disinfection systems involve isolating a device or a set of devices in a box or cart for safety while overdosing the device with UV radiation for fast disinfection. These systems typically utilize high intensity UV energy provided by high power lamps and drivers, which introduces a number of restrictions that make the system undesirable, expensive, and ultimately impractical. Devices are typically physically held in the system by supporting structure associated with the box, cart, or rack. That structure can hide bacteria and pathogens or shield surfaces from being disinfected. If UV dosing is left too low, the device can be more difficult to disinfect or less reliably disinfected. To address these issues some UV disinfection systems deliver more UV energy to ensure UV energy reaches as much of the device as possible. However, this does not always address the issue because portions of the device may be difficult to reach with UV light depending on the position within the rack or the specific physical configuration of the device. Further, the contact areas of the supporting structure may not be treated sufficiently, if at all, which can lead to problems when a user contacts the support structure while retrieving their device.

Some known disinfection systems are integrated into a charging rack so that devices can be disinfected and charged simultaneously. This can make disinfection more difficult and less reliable. For example, it can be challenging to completely disinfect a device due to the physical layout of the charging rack. A disinfection charging rack has additional supporting structure to support the charging functionality that can increase the amount of hidden bacterial or shield surfaces from being disinfected. These systems are not designed for ease of interaction and or intelligent automated interaction. One especially problematic disinfection issue relates to the charging connection point, which can be a source of increased bacterial and pathogen growth. Whether the charging rack utilizes a cord or another type of physical charging connection, manually manipulating the device and the physical charging connection at the beginning and end of a charging session can result in an increased bioburden, with unwanted opportunity for cross contamination and its associated costs. In addition, charging disinfection racks typically involve more repeated and frequent interaction. This increased activity presents the additional challenge of having to reach the full surface area of the devices to provide satisfactory disinfection, while maintaining safety for use in a human filled environment.

As more is learned about the impact of UV energy to devices, more problems and shortcomings of conventional UV disinfection systems become evident. The previous directive of UV disinfection systems that "more is better" when it comes to UV energy has negative ramifications that relate to the destruction or deterioration of materials that were not intended for intense UV exposure. Other issues with known UV disinfection systems include a lack of automation and poor user interface. Known UV systems often require excessive manual intervention by the user and often obscure the process in a way that the user does not understand the charging and disinfection status of the device throughout the process.

SUMMARY OF THE INVENTION

Some aspects of the present invention relate to improvements associated with reducing the spread of infections with a UV transmissive case. A portable electrical device can be installed in a UV transmissive case that provides a UV transmissive layer that enables the transmission of UV energy in a path about the portable electrical device. A three-dimensional UV energy path enables quick and reliable disinfection of externally exposed surfaces of the portable electrical device and case. The UV transmissive case may include a UV reflective substrate to assist with directing UV energy back toward the UV transmission path. Some embodiments of the UV transmissive case may be self-disinfecting, having a UV disinfection control system and UV source integrated within the UV transmissive case.

Other aspects of the present invention relate to improvements associated with reducing the spread of infections with UV disinfection charging systems. UV disinfection chargers can provide both charging power to a portable electrical device as well as UV energy for disinfecting a portable electronic device. Disinfection of the portable electrical device can be provided while simultaneously protecting the user from UV energy. The system can be automated or semi-automated to provide a faster and more controlled disinfection and charging solution for better customer satisfaction. That is, processes related to charging, disinfection, and safety can be automated or semi-automated. A user interface can provide information relating to charring status and disinfection status. Some embodiments of the disinfection charger may include UV transmissive support surfaces that direct UV energy along a UV energy path such that the portable electrical device can be disinfected in a uniform and consistent manner.

The various embodiments of UV transmissive cases and UV disinfection chargers can provide or direct UV energy directed toward harder to reach areas of portable electronic devices, which helps to ensure complete disinfection. That is, some embodiments of the present invention relate to UV transmissive materials and usage, which can address a number of problems related to effective disinfection. Integrating these materials into cases and support surfaces can enable treatment of previously blind surfaces (i.e., a surface or portion of a surface unreachable or unreliably reachable by UV energy) and enable a three-dimensional disinfection solution. For example, some areas of a portable electrical device and some areas of a device case may have areas that are difficult to disinfect, such as the charging port, areas blocked by structure, or areas positioned more distant from the UV source.

Charging Devices

The need to charge mobile devices is a daily requirement. Devices can be charged through an electrical connection or wireless charging. Mobile devices can be charged using a variety of connected solutions from USB to micro USB, USBC, lightning connectors, electrical contacts, or other electrical connections. Devices can be put in environments that are challenging for disinfection because several people throughout the day use the mobile devices.

Indication and Monitoring Feedback

Devices are sometimes charged in charging stations that hold banks of devices. When these banks of devices are charging and new devices are being added and charged devices are being removed, it is valuable to be able to see what is charged and what is disinfected and ready to be used. Some embodiments of the present invention provide a user interface that includes charge status and disinfection status indicators, for example using red and green LEDs, that make it easy and efficient to distinguish when a device is charged and disinfected at a glance.

Stopping Disinfection within Human Proximity

Some past disinfection systems use a box with a lid and when the door is opened the disinfection stops. Some embodiments of the present invention provide improved sensing and interlocks. For example, some embodiments include a sensor system that can monitor one or more of capacitance, motion detection (for example passive infrared ("PIR") or temperature based motion detection), or acceleration movement to shut off or reconfigure the disinfection process. Using low dose UV allows a safe user interface with humans interacting with the charging surface or rack.

360 Degree 3D Protection

Some embodiments include a UV translucent or transmissive material that provide a protective case surrounding the mobile device. The case forms a UV transfer media and allows disinfection about the mobile device, for example about the entire generally cuboid shape of a mobile device. Areas that are blinded to the UV like the bottom of the mobile device can now be disinfected providing 360 degree or three-dimensional ("3D") protection. For mobile devices without cases, UV disinfection chargers can utilize UV transmissive or UV translucent materials on the base with UV treating the bottom of the products. By providing low dose UV projection through a transmissive material, either UV supporting structure or a UV transmissive case, mobile devices can be effectively, efficiently, and safely disinfected.

Control and Interface

Some of the UV disinfection charging system embodiments can detect human activity and use it to control the system. Some embodiments can detect a human even while running near the system. The system can detect human activity using a sensor system, for example including one or more motion, acceleration, capacitance touch, or power sensors to shut off or reconfigure a UV source when a user is present.

The system can track when a device is charging, charging and disinfection time, charge cycles of disinfection and charge status. The mobile device can assist with tracking this information, for example by communicating through an application programming interface ("API") in the mobile device. The mobile device API can track the charge and reports it back to the charger as it relates to the device. The API may be written for the USB connection or via BTLE and can be paired to the charger.

Materials Selection

Plastic injected PFA can be utilized to provide a UV transmissive surface. The plastic injected PFA works with UV-C transmission. In addition, TEFLON can also provide a UV transmissive surface. The thickness of the material is one factor in determining the transmissive capability. The inner surface can be textured to allow scattered reflection. The inner surfaces may also be coated with a reflector to protect the device from UV exposure and also provide a good dispersion and reflection of the UV light. Some embodiments utilize a combination of a textured surface with a reflector coating.

Inside-Out, Outside Projection and Inside Out to Transmitter Substrate and Outside to Transmitter Substrate Multiple embodiments of a UV disinfection system can be provided with various configurations of the UV source according to the present invention. Some of the embodiments include:

A UV source lighting from above that is directed to the device;

A UV source from below the device transmitting UV through a transmissive material;

A UV source above and below where the UV source on the supporting material transmits UV through the transmissive supporting material allowing the bottom to be disinfected properly;

A UV source above where the UV source disinfects the mobile device by first radiating on the device and secondarily transmitting UV through supporting material transmits UV through the transmissive supporting material allowing the bottom or side to be disinfected properly—dependent on mounting; and A UV source disinfecting a case around the mobile device wherein the case distributes the UV to areas around the mobile device for proper disinfection.

Self-Disinfecting Protective Case

Some embodiments of the UV transmissive case can be configured as self-disinfecting by including a disinfecting source and disinfection control system within. It may use the mobile device power or use its own battery. The case may include wireless charging to allow a connecter-less design preventing additional bacteria or pathogen hiding places. The system may use equipment and information from the mobile device such as its accelerometer, battery charge levels, capacitance touch sensor, or it may duplicate these systems within the case for use with the disinfecting system, if desired.

Device Protection

In the past device disinfection cabinets dose the device with UV and UV can break down materials. Some embodiments of the UV transmissive device case according to the present invention include an internal reflector to protect the device while allowing external disinfection.

Motion Interlock

An infrared sensor, such as passive infrared ("PIR") sensor, can be used to detect motion. In addition, an accelerometer can be used to detect acceleration to know when a hand has reached in and when the device moves, is tapped or manipulated. These sensors can be combined with the UV disinfection control system to stop or change operation providing an interlock.

Asset Tracking

An asset tracking component can be included in the UV transmissive case. The asset tracking component can be utilized to provide power and protect the asset tag with the mobile device.

Protective Case and Transmissive Disinfection Media

Some embodiments provide a molded UV transmissive case and a transmissive film being combined to form a protective case and a screen film welded or terminated in a way that enables UV light piping into the screen film. The film can be less than 0.5 mm and in some embodiments less than 0.05 mm, which allows mobile device capacitive touch to work properly.

BRIEF DESCRIPTION OF THE DRAWINGS

FIG. 1A illustrates one embodiment of a UV transmissive case for a smart phone.

FIG. 1B illustrates a sectional view of an alternative embodiment of the UV transmissive case of FIG. 1A cut across section line A.

FIG. 1C illustrates a sectional view of an alternative embodiment of the UV transmissive case of FIG. 1A cut across section line A.

DESCRIPTION OF THE CURRENT EMBODIMENTS

A. UV Transmission Case

Figure 2:
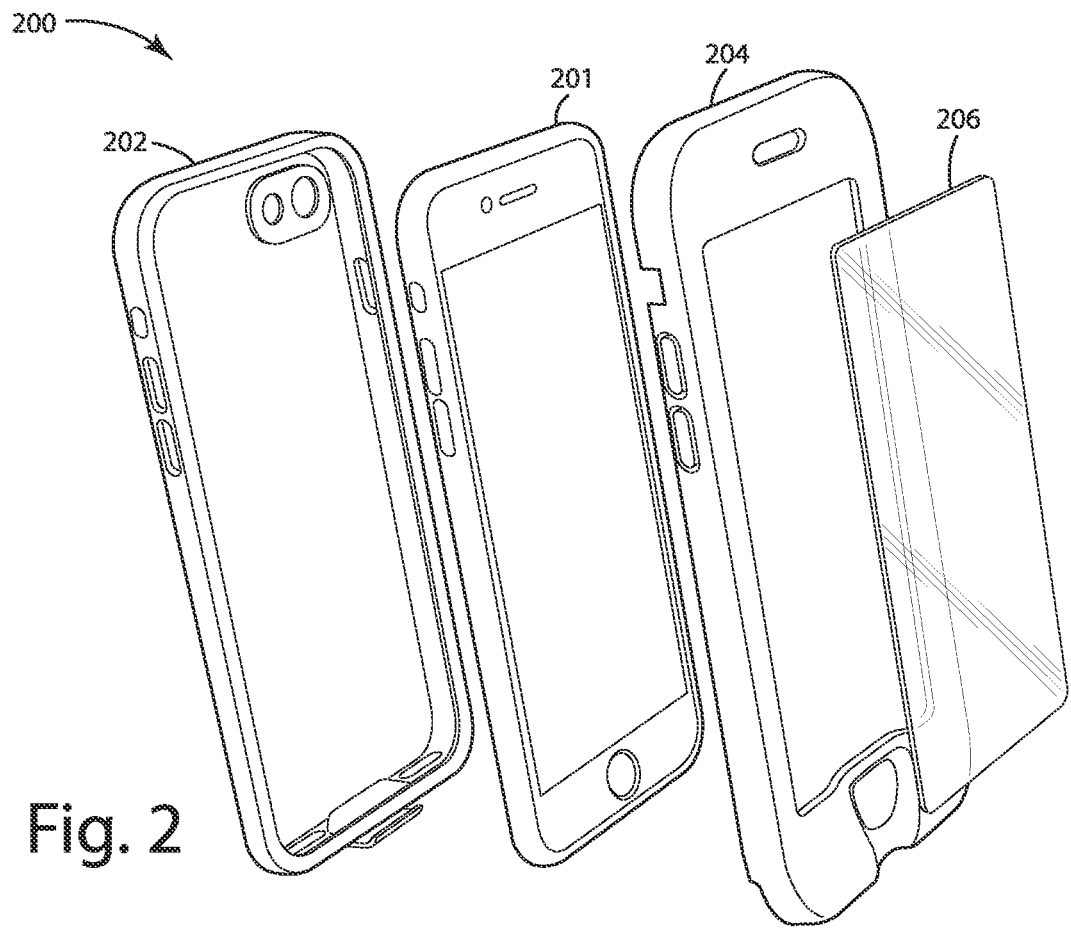
FIG. 2 illustrates an exploded view of an alternative embodiment of a UV transmissive case for a smart phone.

FIGS. 1-5 illustrate multiple embodiments of UV disinfection cases for use with various mobile devices. Each case is configured to assist in the disinfection of a mobile device installed within by facilitating reliable transmission of UV energy from a UV source to the various external surfaces of the mobile device and case assembly.

Each case has a UV transmissive layer or over-layer and an exposed exterior surface that forms a touchable surface of the case. In some embodiments, the exposed exterior surface of the case is the UV transmissive layer. The UV transmissive layer may have a UV transmission percentage of at least 65 percent. Many embodiments utilize UV-C, which typically includes light in the wavelength range of 100 nm to 290 nm. The UV light sources that work in conjunction with various embodiments in accordance with the present invention may be configured to produce UV light at a wavelength of about 254 nm. In one embodiment, the present invention utilizes a UV-C transmissive material having a transmission percentage of at least 60 percent at 254 nm. In another embodiment, the UV transmissive material of the present invention has a transmission percentage of at least 65 percent at 254 nm. In yet another embodiment, the UV transmissive material has a transmission percentage of at least 70 percent or at least about 72 percent. UV fused silica, fused quartz and PFA provide adequate UV-C transmission at 254 nm. Many typical materials, such as Acrylite material, do not pass sufficient UV-C to be suitable for typical applications. The UV transmissive layer may be manufactured from fluoropolymer or perfluoroalkoxy. Each case may include a UV reflective substrate layer. In particular, a case when installed on the mobile device provides a UV transmission system that directs UV light throughout the case to reliably disinfect the exposed surfaces of the mobile device and case assembly. A UV light source may be positioned internally within the case or in a separate, external, UV disinfection system. The UV light source can be positioned adjacent to the UV transmissive over-layer so that UV light is transmitted into and travels along the UV transmissive over-layer progressively exiting over the exterior surface to treat the exterior surface. The reflective layer resists penetration of the UV light into the substrate which not only protects the substrate, and therefore the mobile device being carried by the case, from UV degradation, but also reflects that UV light back into the UV transmissive over-layer where it can contribute to UV treatment of the exterior surface. That is, the UV transmissive over-layer facilitates transmission of the UV light along the over-layer with UV light exiting through the exterior surface. The UV transmissive over-layer may be configured to provide generally uniform escape of UV light and therefore provide generally uniform treatment of the exterior surface. For example, the thickness of the over-layer may diminish away from the UV light source and/or the over-layer may be textured to provide controlled escape of UV light.

For embodiments that include a reflective layer, it may be a thermoplastic substrate disposed below the outer layer with reflective particles as a reflector material. In one embodiment, the present invention may include thermoplastics with enhanced reflectivity to UV-C light. Flow cells that contain e-PTFE (expanded PolyTetraFluor Ethylen) provide 95 percent reflectance or more of the UV-C light—making systems constructed of these materials highly transmissive.

The composition and configuration of the thermoplastic composition and the UV reflective material can be selected to provide a composition with desired levels of UV reflectivity, and transmissivity for a desired application. The composition of the thermoplastic composition may also be selected to be cost-effective, resistant to degradation upon exposure to UV radiation for at least a desired period of time. Utilizing PFA and e-PTFE is a great example of a reflector and UV-C transmissive material. Further details and examples of UV reflective material appropriate for use in the present invention are described in U.S. provisional patent application 62/650,340, entitled Disinfection Behavior Tracking and Ranking, filed on Mar. 30, 2018 to Baarman, which is incorporated by reference in its entirety.

A device may include a fluoropolymer, such as perfluoroalkoxy ("PFA"), over layer as a light-pipe to transmit UV-C 254 nm light over that touchable surface. A DuPont Teflon can be used but some good results have been with Daikin NEOFLON PFA AP201SH, a copolymer of tetrafluoroethylene and perfluoroalkylvinylether. It is a perfluoropolymer consisting of only carbon atoms and fluorine atoms without any hydrogen atom.

Figure 3:
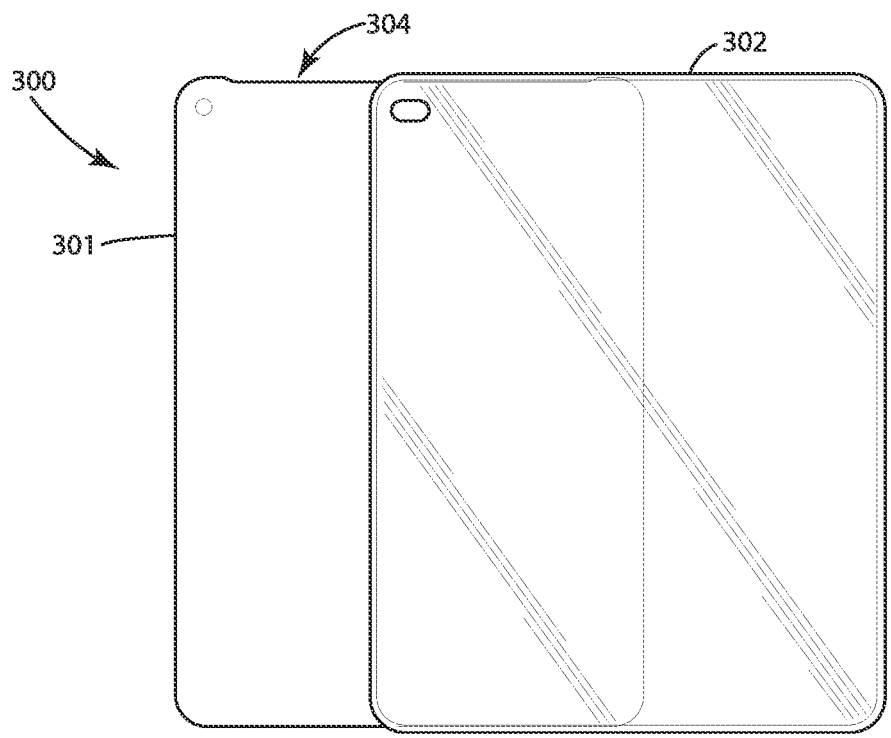
FIG. 3 illustrates an embodiment of a UV transmissive case for a tablet.

The case can be in the form of a variety of different constructions. Several different embodiments of a UV transmissive case for a smart phone are shown in FIGS. 1-2. FIG. 3 shows a UV transmissive case for a tablet.

Referring to FIG. 1A, a UV transmissive case of one embodiment is depicted. The case includes three snap together elements: front and rear enclosures 102, 104, and a screen film 106. In alternative embodiments, the front and rear enclosures may be provided as a unitary construction allowing for friction fit of the mobile device. Or, as another alternative, the enclosures may be fastened together other than by snap-fit, for example, through the use of mechanical fasteners. In the depicted embodiment, these three elements surround the device for protection and enable UV disinfection distribution throughout the three-dimensional surface.

The case 100 depicted in FIG. 1A includes a disinfection translucent plastic housing 102, 104 with a screen cover 106 in the form of a UV transmissive film. The disinfection translucent plastic housing 102, 104 includes a UV reflective substrate layer and a UV transmissive over-layer, as described above.

The UV reflective substrate layer can be configured as some or all of the device-facing surfaces of the case. That is, the device-facing surfaces of the case 100 may be textured and coated with a UV reflective material such as Polytetrafluoroethylene ("PTFE"), titanium dioxide ("TiO2"), or aluminum. The UV reflective material may have UV reflective properties and/or UV absorbent properties. The surface can be accomplished by plating a substrate with the UV reflective materials, electrical coating, painting a substrate with the UV reflective material, or otherwise applied to a substrate. The various surface treatments can be applied to all sides of the substrate or to just one side of the substrate.

The arrangement of the housings 102, 104 and screen cover 106 can perhaps be best understood with respect to the sectional view illustrated in FIG. 1B. The sectional view illustrates how the housings 102, 104, once snap fit or otherwise assembled provide an enclosure with a UV transmissive layer 122, a UV reflective substrate 120, and an optional finished layer 124 forming the majority of the external surface of the case. In the current embodiment, the mobile device 101 is friction-fit against the inner-housing. Specifically, the mobile device 101 is friction fit against the UV reflective substrate 120. The screen film 106 snaps into place over the touch screen of the front of the mobile device 101. UV light or energy that makes contact with the UV transmissive layer 122 is guided by the layer 122 along the three-dimensional space around the device. Because the screen cover 106 is itself UV transmissive and the UV transmissive layer 122 are arranged in optical connection, UV energy traveling through the transmissive layer is urged to travel along the screen film 106 and disinfect that surface. FIG. 1C shows an alternative embodiment in which once the housings 102, 104 are snapped together the finish layer 124 does not wrap around the back of the mobile device. Instead, only the UV transmissive layer 122 and UV reflective layer 120 wrap around the sides and back of the device. The finish layer 124 is provided only along the peripheral edge of the mobile device. In this configuration, the finish layer 124 may be a non-UV transmissive surface because when the device is placed on a UV charging rack or on a UV disinfection charger the UV energy will not need to penetrate the finished coating 124 to reach the UV-transmissive layer 120 and be transmitted along the UV energy path wrapping 360 degrees around the device providing three-dimensional disinfection.

Referring back to FIG. 1A, the housings 102, 104 generally surround the mobile device 101 with the main exception of the screen area, which is covered by the screen cover 106. The housing also includes additional apertures and buttons to facilitate various features of the mobile device, such as a volume control housing feature 110, a power control housing feature 112, speaker housing feature 114, a camera housing feature 116, and a power connection housing feature 118. The UV transmissive layer 122 surrounds these features and directs UV energy toward them such that these features receive a satisfactory dose of UV energy and are thereby disinfected.

Figure 12:
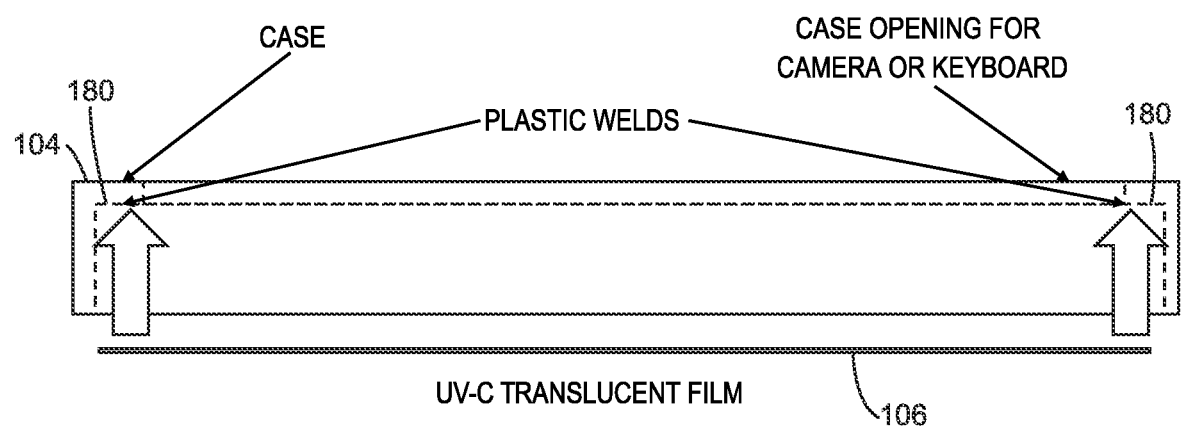
FIG. 12 illustrates a sectional view of the UV transmissive case of FIG. 1A cut across section line A depicting the installation of a UV-C translucent or transmissive film.

The thickness of the UV transmissive film 106 can vary depending on the application. In the current embodiment, the thickness is less than 0.5 mm to enable the capacitive touch features of the mobile device screen while piping UV light to the mobile device screen. In alternative embodiments, the thickness can be 0.05 mm or less and still enable the capacitive touch features of the mobile device screen while piping UV light to the mobile device screen. The screen film 106 can be optically and mechanically or otherwise physically joined to the case housing 102, 104 or to the mobile device 101. Specifically, the screen film 106 can be attached to the housing along its periphery near the front housing with polished surfaces to allow UV to freely enter the edge of the film, perhaps as best shown in the FIG. 12 sectional view. The UV transmissive film 106 can be joined to the front enclosure and/or the mobile device 101 itself through a variety of well-known techniques. For example, as depicted in FIG. 12, the UV transmissive film 106 may be plastic welded to a portion 180 of the interior surface of front housing 104. By joining the screen film 106 to the case in this way, optical communication between the UV transmissive screen film 106 and the UV transmissive case can be enabled. The front enclosure can have the screen film 106 pre-welded such that when the front enclosure and back enclosure are fitted around the mobile device, the screen film 106 is adjacent the touch screen of the mobile device 101. Alternatively, the screen film 106 can be provided as a separate component to be mounted by the user to the mobile device 101 or case 100 through a variety of dry or wet mount techniques. For example, in one alternative embodiment, the film can be provided on a substrate with one side having an adhesive for adhering directly to mobile device 101 or portion 180 of case 100.

FIG. 2 illustrates another embodiment of a UV transmissive case. The exploded view of FIG. 2 illustrates a rear portion of the disinfection translucent plastic case 202, a front portion of the disinfection plastic case 204, the disinfection translucent film 206, and a mobile device 201 capable of installation in the case. The front portion 204 of the case and the rear portion 202 snap fit together to enclose the mobile device 201. The disinfection translucent film snap fits along the edge of the opening in the front portion 204 of the case. As assembled, the components provide a disinfection translucent plastic case 200.

FIG. 3 shows another embodiment of a UV transmissive case. The case is similar to the cases depicted in FIGS. 1-2, but is specifically constructed for a tablet device. The disinfection translucent plastic case 300 includes a rear housing portion 302 and a front housing portion 304 along with a disinfection translucent film (not shown), which covers the touch screen (not shown) of the tablet 301. The rear housing portion 302 and front housing portion 304 cooperate to encase the tablet with a UV transmissive surface that guides UV light throughout the UV transmissive housing and also directs UV light toward the disinfection translucent film. Alternative embodiments for essentially any mobile device can be constructed such that the device is encased with a housing having a UV reflective substrate layer and a UV transmissive over-layer that facilitates the transmission of UV light to disinfect the device and the case.

Figure 5:
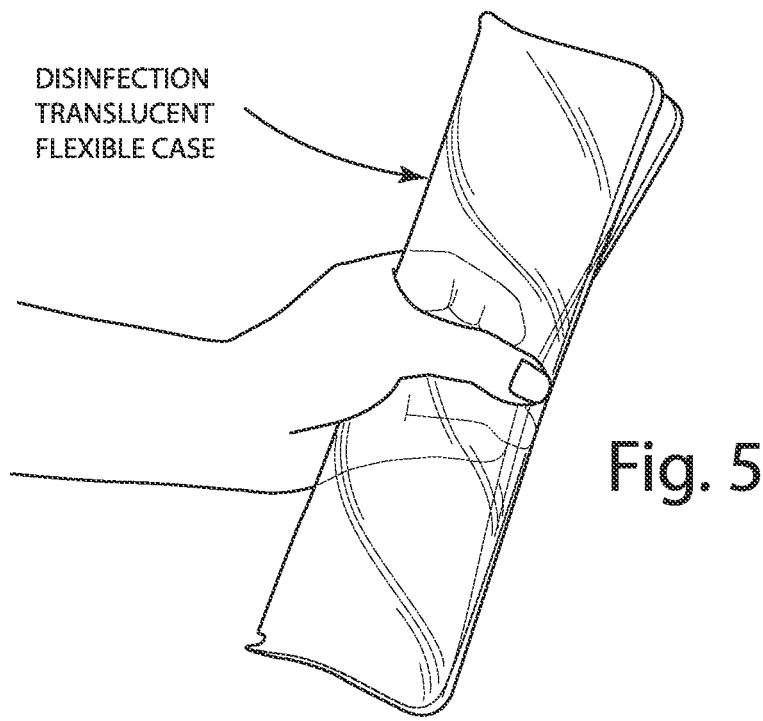
FIG. 5 illustrates one embodiment of a flexible UV transmissive cover.

FIG. 5 shows an embodiment of a flexible UV transmissive case for disinfection. The arrangement of UV transmissive and UV reflective substances is similar to that of the UV transmissive cases discussed above. However, the materials upon which these substances are applied are a flexible material that is manually pliable such that the bag can fit a multitude of different size and shaped devices. For example, the bag can be made of polyvinyl chloride ("PVC") or another flexible plastic material. The amount of flexibility of the bag can be adjusted via the addition of plasticisers, which is a substance added to a synthetic resin to produce or promote plasticity and flexibility and to reduce brittleness. The UV transmissive and UV reflective material can be plated, coated, painted, or otherwise applied to the flexible material.

The flexible UV transmissive case is configured as a bag that includes UV transmissive material. The bag includes an opening for inserting a portable electrical device and may include a closure, such as a zip-lock, snaps, or a drawstring. For example, a slider can travel along a chain to zip the enclosure open and shut. The closure can create a seal or merely close the bag sufficiently such that the device does not easily fall out of the bag. In use, the portable device is slid into the bag and the bag is closed. When placed near a UV source, because the bag includes UV transmissive material, as the UV energy engages the bag, the walls of the flexible bag act as a light piping surface that disperse the UV energy throughout the walls of the bag, disinfecting the various nooks and crannies formed as the flexible bag sits near the UV source. The UV transmissive walls of the bag, when combined with the UV reflective substrate disposed beneath the UV transmissive layer, creates a UV energy transmission path in three-dimensions around the portable device that disinfects the entire surface of the bag. This lower cost UV transmissive enclosure can be used with almost any portable device. It allows rapid adaptation and use with a multitude of devices and to be formed and manufactured easily, adapting this to scanners, radios, phones and other devices quickly.

A UV transmissive case may incorporate UV disinfection circuitry thereby providing a self-disinfecting UV transmissive case. The UV disinfection circuitry can allow the case to self-disinfect the portable electrical device installed in the case. The UV disinfection circuitry can be specifically disposed and configured to provide UV energy along a UV transmission path about the portable electrical device. For example, FIGS. 4A and 4B illustrate one embodiment of a self-disinfecting UV transmissive case 400 including a UV disinfection circuitry 402 and UV source(s) 404.

Figure 4A:
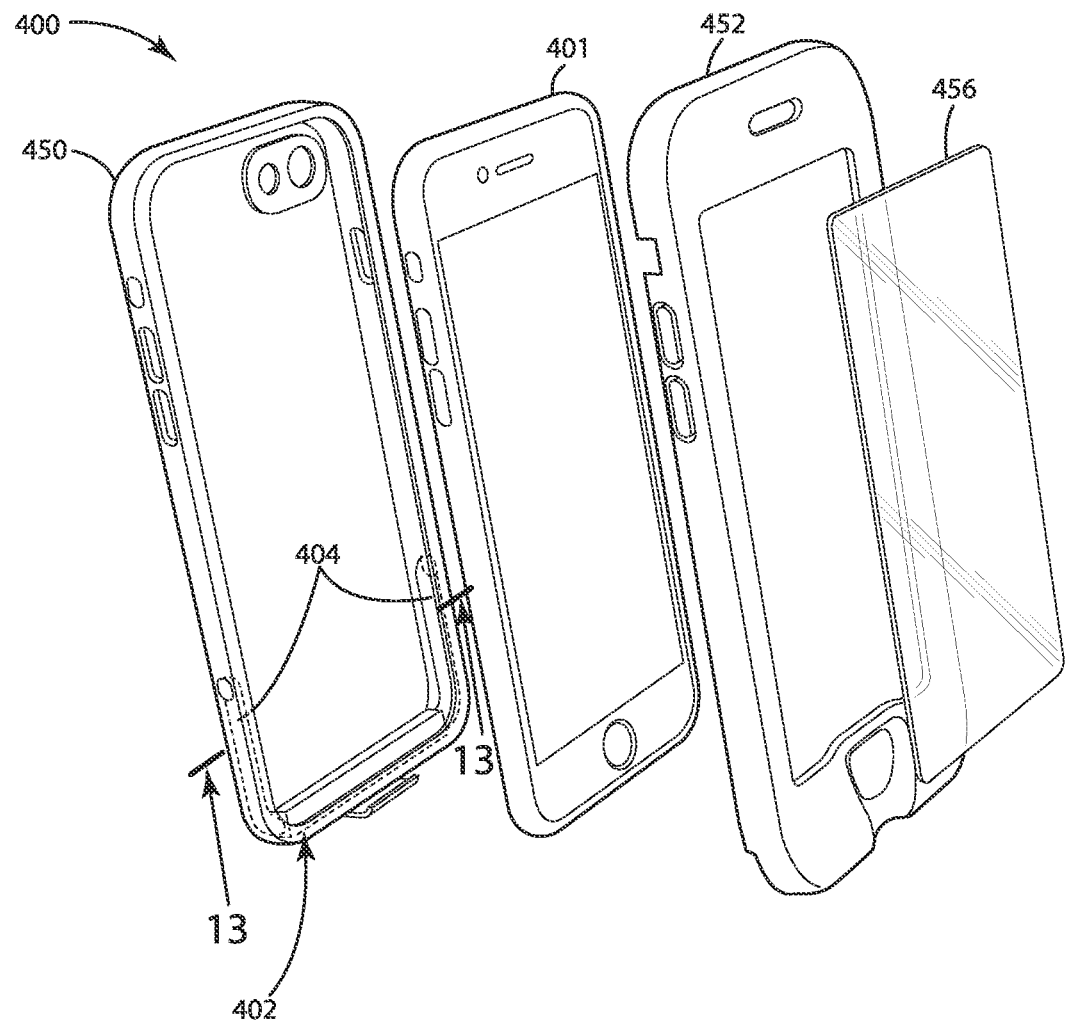
FIG. 4A illustrates an exploded view of one embodiment of a self-disinfecting UV transmissive case.
Figure 4B:
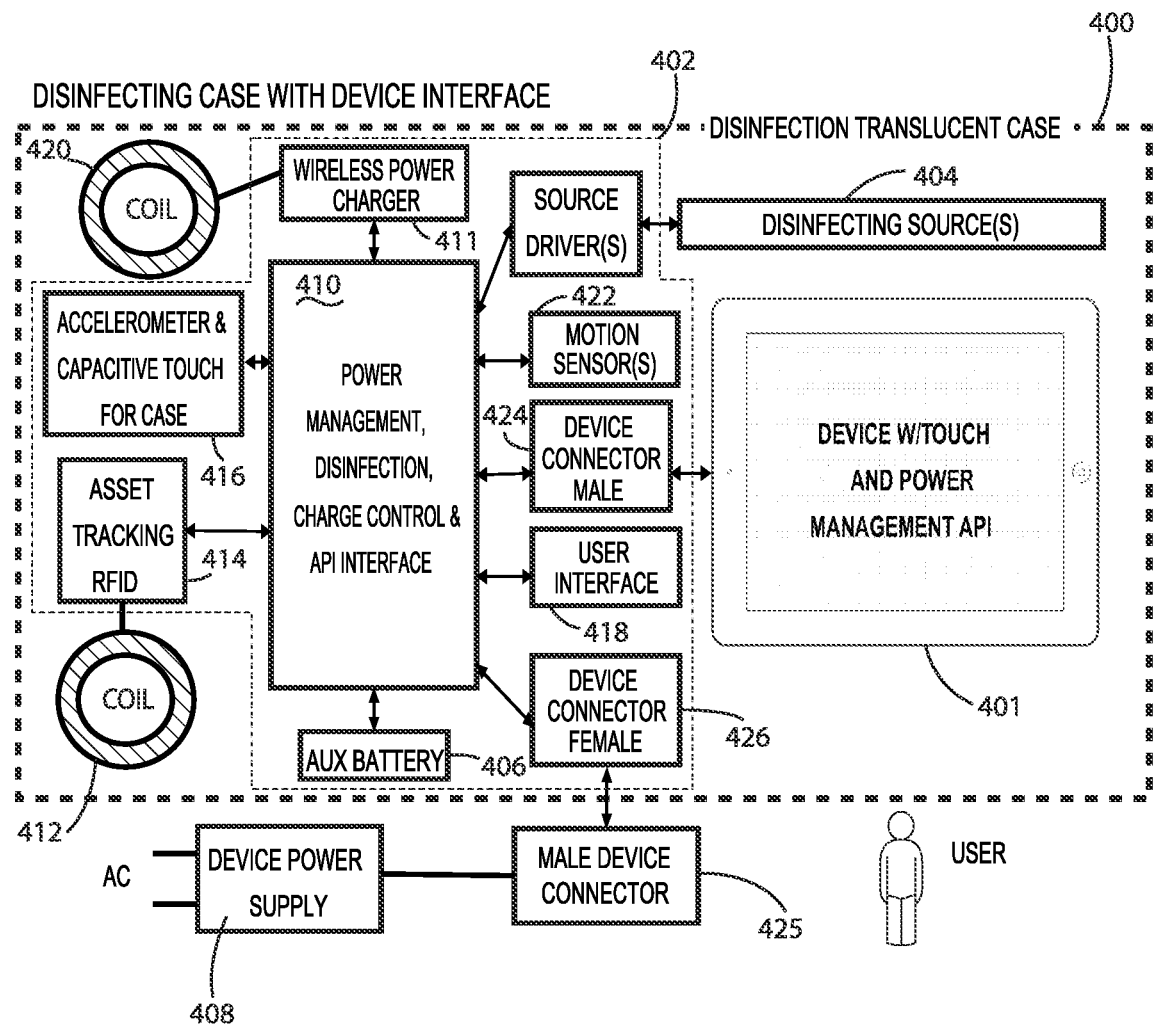
FIG. 4B illustrates a representative block diagram of circuitry of one embodiment of a self-disinfecting UV transmissive case.

FIGS. 4A and 4B illustrate an exemplary control system for a self-disinfecting UV transmissive case 400 for a mobile device. The depicted embodiment includes the features of the UV transmissive case described above and in addition includes components for carrying out disinfection using one or more disinfection sources 404 installed in or on the case. The self-disinfecting UV transmissive case may also include various components for tracking the status and progress of the disinfection process. Alternative embodiments may include some or all of the depicted components depending on the desired functionality.

Referring to FIG. 4B, a representative block diagram illustrating one embodiment of the circuitry for a stand-alone or self-disinfecting UV disinfecting case is illustrated. The case can be powered by the battery of the mobile device 401 via connector 424, an auxiliary battery 406 disposed within the case, or from an external wired power supply 408 via electrical connectors 425, 426 or wireless power supply (not shown) via coil 420. The case may be configured not to utilize device power. The case can include a controller 410 with various functionality such as power management, disinfection control, charge control for wired or wireless charging 411, and an application programming interface. The case can include asset tracking circuitry, such as an RFID coil 412 and associated RFID circuitry 414. The case can also include an accelerometer 416 and/or other motion sensor 422, and user interface 418. One or more wireless power coils 420 can be located within the case and can be completely intrinsic and water tight for cleaning.

Figure 13:
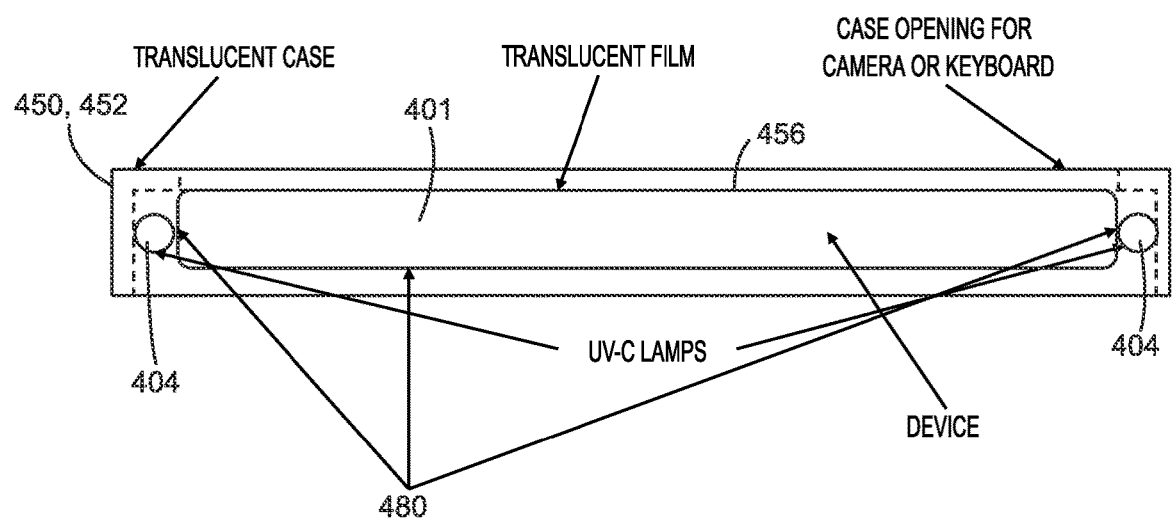
FIG. 13 illustrates a sectional view of an alternative embodiment of the UV transmissive case of FIG. 4A cut across section line B.

The self-disinfecting UV transmissive case may include a pocket for the various components, including the electronics, battery, UV source(s), and wireless power circuitry. Referring to FIG. 4A, in one embodiment, the majority of the components 402 can be disposed near the power input, while the disinfecting sources 404 are disposed along the edge of the case positioned to transmit directed UV energy along the UV transmissive layer of the case 401, which will disperse along the UV energy path provided by the UV transmissive material located in the front and rear enclosures 450, 452 and the UV transmissive film 456. The arrangement of the device 401, transmissive housing 450, 452, disinfecting sources 404, UV reflective coating 480, and UV transmissive film 456 are illustrated in the section view of FIG. 13 cut along sectional line of FIG. 4A. As depicted, the UV sources are disposed within the case between the UV transmissive layer of the housings and the UV reflective coating 480 disposed on the interior surface of the housing 450, 452. As UV light emits from the UV sources, it is transmitted along the UV transmissive material of housings 450, 452 while the interior reflective coating 480 directs UV light back into the UV transmissive housing 450, 452. The UV light is also transmitted across the thin UV transmissive film 456 disinfecting that surface.

Figure 14:
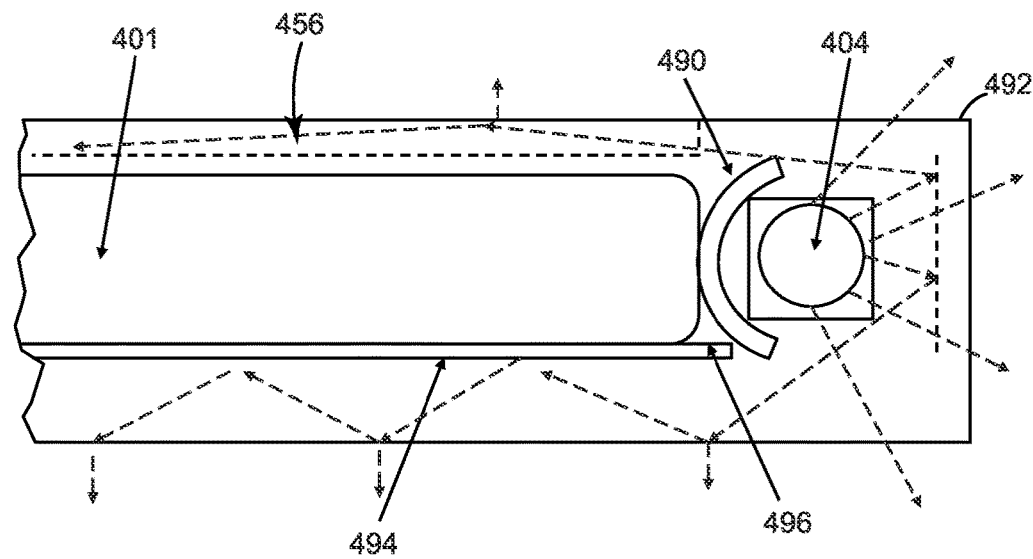
FIG. 14 illustrates a partial sectional view of an alternative embodiment of the UV transmissive case of FIG. 4A cut across section line B.

FIG. 14 provides an exemplary depiction of the travel of light within a UV transmissive material. In the current embodiment, the depiction is shown within the context of a UV transmissive case, but it should be understood that the same principles apply to the UV supporting structure described in connecting with the UV disinfection charger embodiments. Referring to FIG. 14, the UV source 404 can emit light in an omni-directional or directed fashion. In the depicted embodiment, a concave UV reflector 490 is positioned between the device 401 and the UV source. The reflector 490 reflects UV light away from the device and toward the edge of the case where it contributes to disinfecting the exterior surface 492 of the case. As depicted, some of the UV light refracts and travels along the UV transmissive case material, including along the UV transmissive film 456. In this way, the UV light travels 360 degrees around the device and surrounds all three-dimensions of the surface of the device. The depicted embodiment includes two additional optional features. First, the sides and bottoms of the interior surface of the UV transmissive layer are textured 494 for UV light dispersion. The texture pattern can be essentially any pattern that provides the desired UV light dispersal. Second, a UV reflective coating or layer 496 may be provided adjacent the textured pattern for reflecting the UV light back toward the exterior surface 492 of the case.

Optically, the use of texture can provide better piping and performance by creating multiple light paths. The substrate may include a structural thickness for strength and reduced thickness to provide better UV transfer with less loss. Thickness is directly proportional to UV-C losses with materials with lower transmissivity. Providing scratches, a gradient of prism-like surfaces or a simple texture, the system can extract light from the material. Without this modification of the material, light will have a tendency to exit in the directed pattern. An example of this is, when projected through a material, the texturing diffuses the light. To illustrate, when edge light is projected into a piece of quartz, there is great edge to edge transmission but little surface emission. If the quartz is textured or there is a reflector with UV reflectivity, good transmission is achieved. In some applications, the substrate may include textures for indirect source pick up and polished surface for direct source areas. Texturing and polishing a substrate using a flaming process may provide enhanced performance.

The system is designed to enable wireless power or connected power based on a user's request or desire. That is, the system can recognize when power is connected to connector 426 and use that power to operate the disinfection system, pass-through power to the device 401, and/or charge the auxiliary battery 406. The system also can include a device interface including a universal serial bus ("USB") port and/or Bluetooth Low Energy ("BTLE") capability to connect to a device application programming interface ("API") for communications and monitoring of power, charging status, acceleration sensors and touch interface. These and other capabilities can be implemented as described in U.S. provisional patent application 62/650,340, entitled Disinfection Behavior Tracking and Ranking, filed on Mar. 30, 2018 to Baarman, which is hereby incorporated by reference in its entirety. Through the use of communication and external processing, the circuitry positioned in the self-disinfecting case may be reduced.

The case 400 may include a user interface 418 with one or more indicators that can indicate disinfection status. For example, an indicator that flashes red when the device is dirty and disinfection is advisable, blue while disinfection is in process, and green to indicate the device is clear.

The disinfectant transmissive translucent case enables the case to be used to deliver this indication when and where needed. For example, the control system can determine when the device stops moving and the user is not present using a combination of motion and presence detection. Then, when the device is set down the UV disinfection cycle starts and the proper dose is delivered. The system monitors motion and can reset the disinfection cycle if significant motion is detected sufficient for the system to determine a user is present and start the process all over again. In this way, the self-disinfecting transmissive case can disinfect after each use and prepare the device for the next use automatically. By equipping this case with circuitry for reception of wireless power a connector or adaptor enables an electrical connection to the device power connector, which in turn allows for charging the device using wireless power supplied to the disinfecting case. This reduces areas that can hide bacteria and pathogens by limiting the amount of connectors and cords, which tend to represent areas of increased bioburden.

B. UV Disinfecting Chargers

Some embodiments are directed to a disinfecting charger with a monitoring and safety system that utilizes user detection and sensors to detect proximity and provides user feedback on safety, disinfection and charge status. The charger may include a UV transmissive material designed enable disinfection of hard to reach surfaces safely. This disinfecting charger can include an automatic interlock to protect users from UV exposure and can log the exposure limits vs. actual exposure. The system can be a cloud based system that enables a safer ecosystem and cross statistic sharing of safety parameters.

Figure 8:
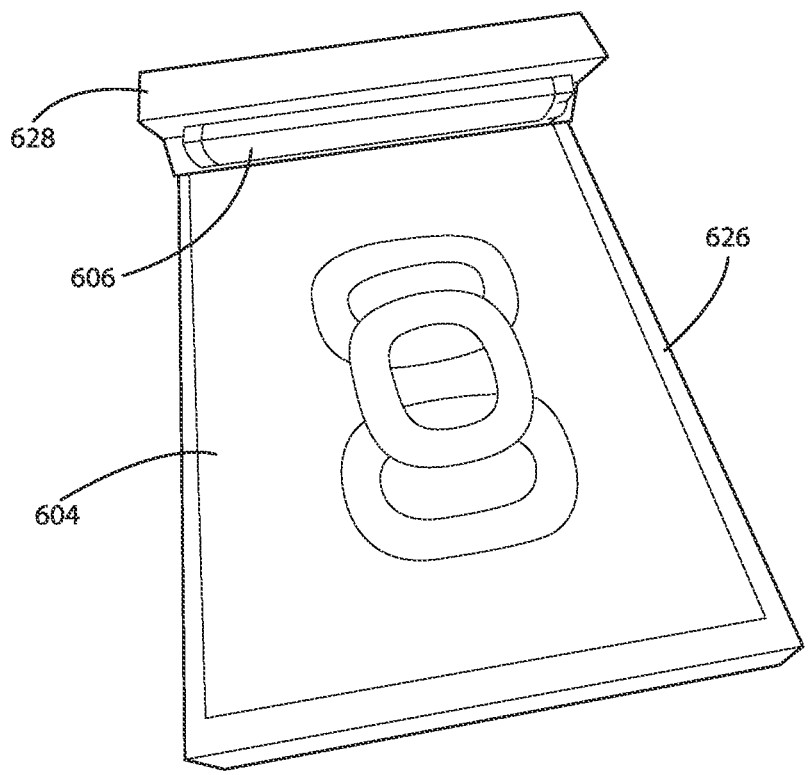
FIG. 8 illustrates a top view of the UV disinfection charger of FIG. 7.
Figure 9:
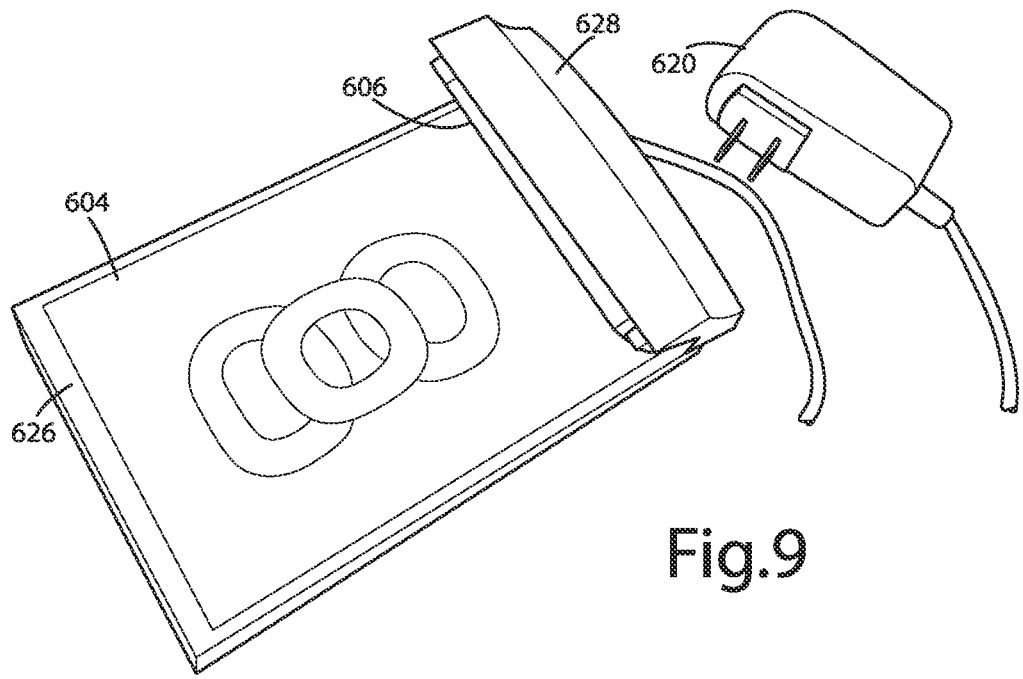
FIG. 9 illustrates a top view of the UV disinfection charger of FIG. 7 and the wall mount power supply.
Figure 10:
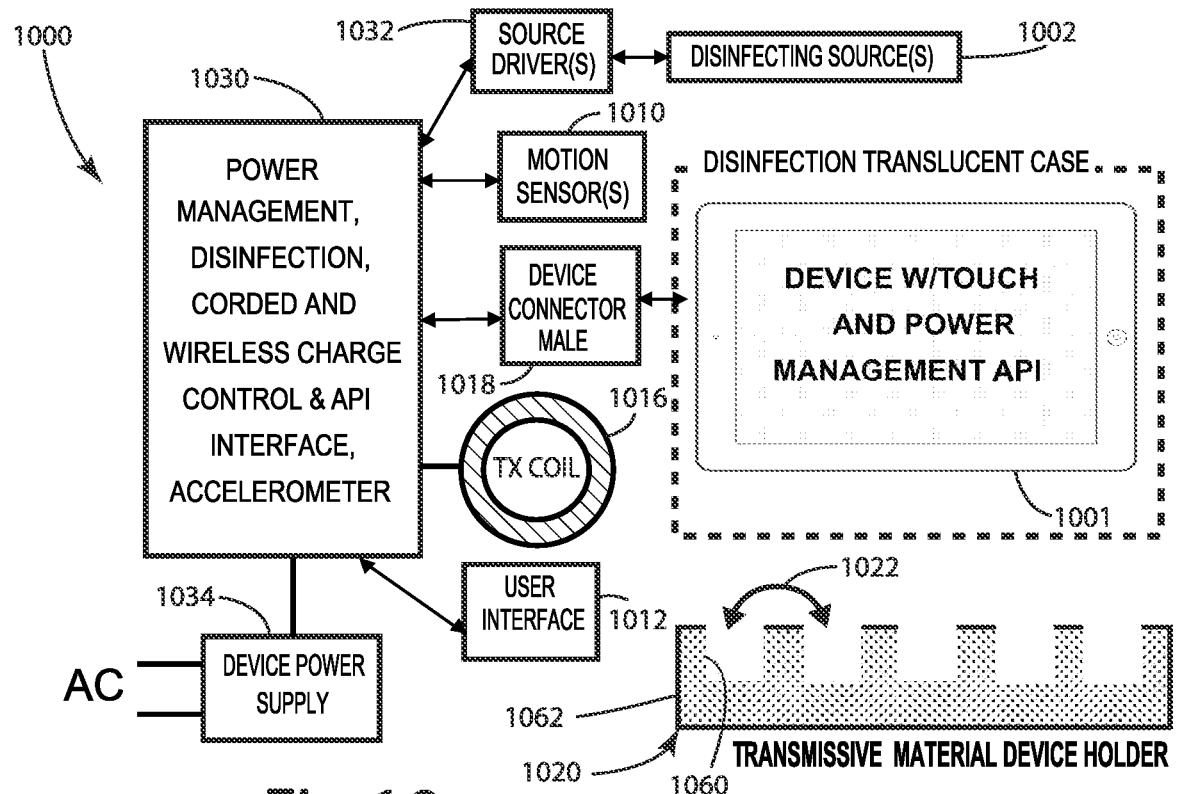
FIG. 10 illustrates a representative block diagram for a UV disinfection charging cabinet or rack.
Figure 11:
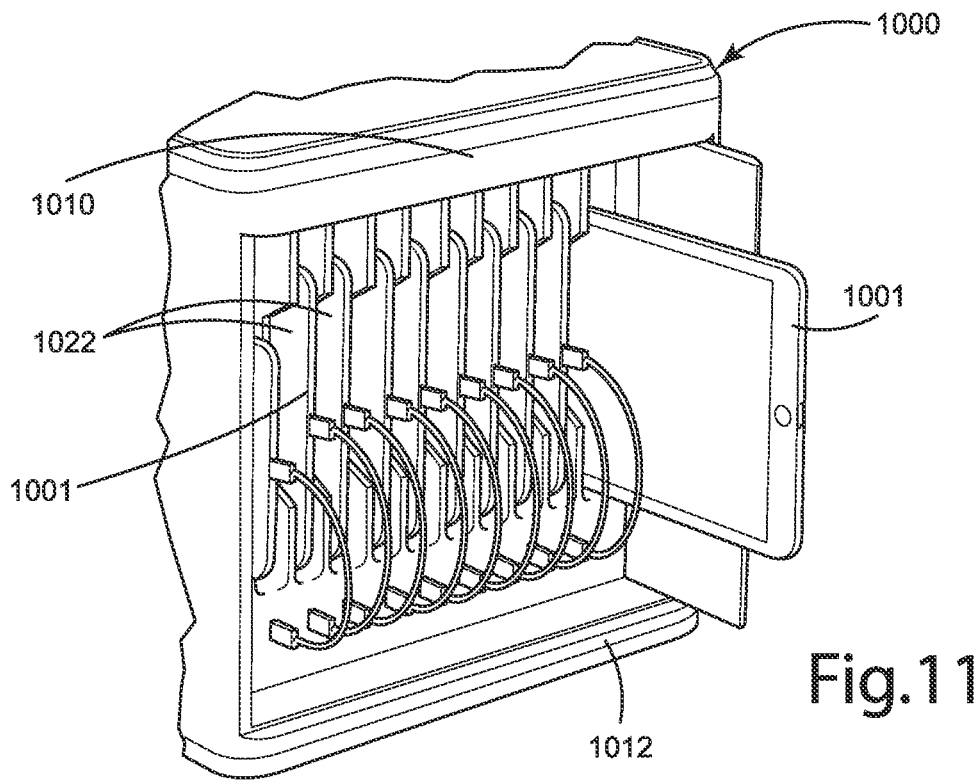
FIG. 11 illustrates a perspective view of one embodiment of a UV disinfection charging cabinet with indicators and motion detection.

FIGS. 6-9 illustrate a first embodiment of a UV disinfection charger and FIGS. 10-11 illustrate a second embodiment of a UV disinfection charger. A UV disinfection charger of the present invention can be configured for use with essentially any device or device case. That is, a UV disinfection charger in accordance with an embodiment of the present invention can include a UV source for transmitting UV energy toward the device or device case in order to disinfect a portable electrical device and/or case for that device and in addition provide power to the portable electrical device, simultaneously or at different times. For example, some embodiments of UV disinfection chargers according to the present invention can work in conjunction with any of the UV transmissive cases discussed above. Alternatively, some embodiments of UV disinfection chargers can disinfect a device without a UV transmissive case, or without a case at all.

Figure 6:
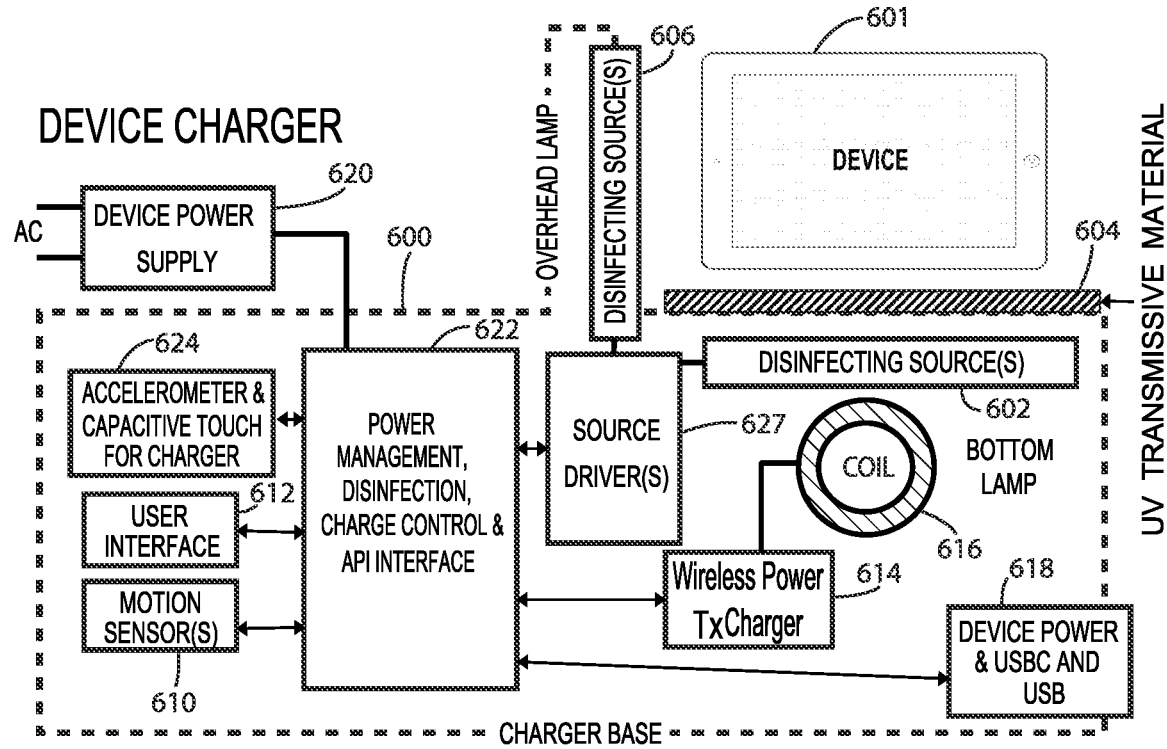
FIG. 6 illustrates a representative block diagram of a UV disinfection charger.
Figure 7:
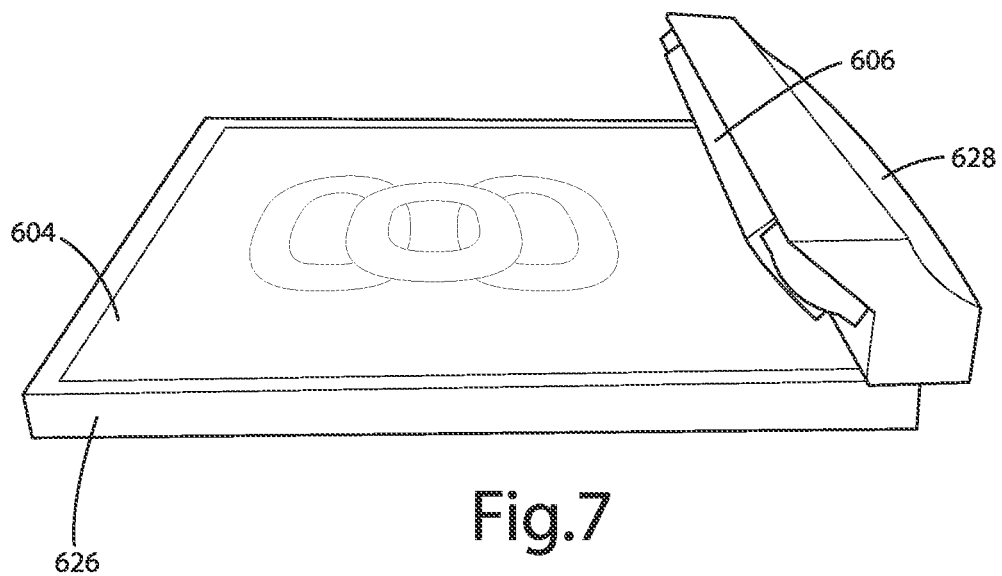
FIG. 7 illustrates a side perspective view of a UV disinfection charger with a UV transmissive material supporting the back of the mobile device.

FIG. 6 illustrates one embodiment of a representative block diagram for UV disinfection charger 600. The device 101 sits on a UV translucent or transmissive surface 604 with optional UV sources underneath. One or more charging coils 616 are provided for wireless charging. The system can detect when a device is placed on the surface using the wireless charging circuitry 614 and coil 616. The system uses multiple interlocks to detect movement, acceleration, and charging to disable or change operation of the UV disinfection system when the user is touching, or determined to be within proximity of the device. This triggers a timing loop that waits for a predetermined amount of time and then re-starts the disinfecting cycle. If motion is detected the disinfection cycle is delayed and an indicator is set to indicate that the device has not been disinfected. The depicted charger also includes an overhead UV source 606 to disinfect the top side of the device as shown in FIGS. 7-9.

The depicted embodiment includes both a bottom UV source 602 disposed under the charging surface and a top UV source 606 configured to shine UV light on the top of the portable electrical device being disinfected. The charging surface includes a UV transmissive support material 604 to support the device 601 being charged while disinfecting the bottom and sides from the bottom. The charger 600 can include protection interlocks that detect physical motion and infrared movement, for example with one or more motion sensors 610. These motion sensors 610 can be used to interrupt the disinfecting sources when motion is detected and enable the disinfection cycle to begin or start over when there is a lack of motion for a predetermined amount of time. The charger base 600 may include a user interface that includes various indicators that represent the status of charging, the status of disinfection, the presence of a user, or a variety of other information. For example, a disinfection status indicator can turn an indicator light red when disinfection is advisable, blue while disinfection is in progress, and green when disinfection is complete and the device is clean.

The embodiment depicted in FIG. 6 includes wireless power circuitry in the form of a wireless power transmitter circuit 614 and coil 616. The depicted embodiment also includes one or more USB and USBC ports 618 to charge single or multiple devices using cords. In alternative embodiments, the UV disinfection charger may accommodate only wired charging but not wireless charging, or vice versa.

The size of the charging surface can vary depending on the application. Perhaps best shown in FIGS. 7-9, the UV transmissive support surface 604 of the current embodiment is sized to hold a smart phone, but can be enlarged to 15" by 15" or larger, depending on the application. For example, a larger area may be desirable if the charger will hold multiple devices, tablets, or radios. The dimensions of the charging surface can be sized to accommodate whatever size devices is appropriate and the charger can also provide multiple wireless chargers and USB/USBC type connectors for versatility of use. The UV disinfection charger 600 can be supplied power by a device power supply 620, such as a wall adapter 620 connected to a main power line. Alternatively, the UV disinfection charger 600 may be powered by a battery or other power source.

The UV disinfection charger 600 can include a controller 622 that is programmed to provide various functionality such as power management, disinfection control, charge control for wired or wireless charging, and an application programming interface. The controller 622 can communicate with the sensor system of the UV disinfection charger, which can include a variety of sensors, for example, motion sensor 610, user interface 612, accelerometer 624, and other sensors depending on the application. Further, the controller 622 can operate the source driver(s) 627, which drive the UV disinfecting sources 604, 606.

FIGS. 7-9 illustrate various views of the UV disinfection charger 600. FIG. 7 shows a perspective side view, FIG. 8 shows an overhead view, and FIG. 9 shows a view including the wall mount power supply 620. One UV source is located under the UV transmissive supporting structure 604 and one UV source 606 is located in an angled portion of the housing 628 oriented to shine UV light on the top of a mobile device set on the UV transmissive supporting structure 604. The bottom UV source 606 is positioned under the UV transmissive supporting structure 604 such that it shines UV light on to the UV transmissive supporting structure 604 which guides the UV light along a path about the mobile device such that the UV light penetrates through the UV supporting surface 604 reaching the bottom of a mobile device set on the charging surface and also reaches the sides of the mobile device. Together, the two UV sources and UV transmissive supporting structure cooperate to provide UV energy to the three-dimensional surface of a mobile device set on the UV transmissive supporting structure 604 of the UV disinfection charger 600.

FIGS. 10-11 show an alternative embodiment for a UV disinfecting charger in accordance with the present invention. This embodiment provides a cabinet configuration, in which multiple portable electrical devices can be installed and simultaneously charged/disinfected.

FIG. 10 illustrates a representative block diagram of a control system for a cabinet or rack mounted charging and disinfection system 1000. The system 1000 can provide the same user protection and low dose disinfecting light source as discussed in connection with the UV disinfection charger 600. The rack can include wireless power and several USB charging ports for multi-device charging and disinfection. The cabinet includes a user interface for efficiently and easily informing users about the disinfection and charging status of the devices on the rack, and also includes a transmissive rack assembly, also referred to as a UV transmissive support structure 1020.

The control system 1000 operates similarly to the control system of UV disinfection charger 600. The system 1000 includes one or more disinfecting sources 1002 configured to shine UV light toward the portable electrical device(s) being disinfected. The cabinet 1000 may include protection interlocks that detect physical motion and infrared movement, for example with one or more motion sensors 1010. These motion sensors 1002 can be used to interrupt the disinfecting sources 1002 when motion is detected and enable the disinfection cycle to begin or start over when there is a lack of motion for a predetermined amount of time. The cabinet 1000 may include a user interface 1012 that includes various indicators that represent the status of charging, the status of disinfection, the presence of a user, or a variety of other information. For example, a disinfection/charging status indicator for each portable electrical device slot can turn an indicator light red when charging or disinfection is advisable, blue while disinfection or charging is in progress, and green when disinfection and charging are complete. Separate indicators for charging and disinfection may also be provided. For example, a charge status indicator can indicate red for no device present, yellow for partially charged, and green for fully charged. For the disinfection status indicator an indicator can emit red light when disinfection is advisable or no device is present, blue while disinfection is in progress, and green when disinfection is complete. In this way, the status indicators can allow a user to easily select a device from the cabinet based on disinfection safety and charge status.

The UV disinfection charger 1000 can include a controller 1030 that is programmed to provide various functionality such as power management, disinfection control, charge control for wired or wireless charging, and an application programming interface. The controller 1030 may include an integrated accelerometer or connection to an accelerometer or other sensors that make up part of a sensor system, which can be used to provide various inputs to the control system. The controller 1030 can communicate with the sensor system of the UV disinfection charger, which can include any integrated sensors, as well as any external sensors such as motion sensor 1010, user interface 1012, and other sensors. Further, the controller 1030 can operate the source driver(s) 1032, which drive the one or more UV disinfecting sources 1002. The UV disinfection charger 1030 can be supplied power by a device power supply 1034, such as a wall adapter 1034 connected to a main power line. Alternatively, the UV disinfection charger 1034 may be powered by a battery or other power source. The controller 1030 may be capable of transmitting wireless power through one or more transmitter coils 1016. The cabinet may also include one or more charging ports 1018 to charge single or multiple devices using cords. In alternative embodiments, the UV disinfection charger may accommodate only wired charging but not wireless charging, or vice versa.

The UV disinfection charger 1000 of the current embodiment is configured for use with either devices installed in UV transmissive cases, a UV transmissive rack or device holder 1022, or a combination of both. This UV transmissive material assists in ensuring that disinfection is compete and that UV energy reaches the three-dimensional space surrounding the external surface of each portable electrical device as well as any cabinet surface that is susceptible to human touch during normal operation. Various embodiments of UV transmissive cases are discussed above at length and therefore will not be discussed in detail here. Suffice it to say, many of the same principles discussed in connection with the UV transmissive case apply to the UV transmissive support structure 2020 that holds portable electrical devices. The exemplary plan diagram of holder 1020 depicted in FIG. 10 shows an example of how a UV transmissive surface that acts as a light pipe enables UV light to reach the three-dimensional area surrounding the portable electrical device held in a slot 1022 of the holder 1020.

The UV transmissive support structure 1020 is lined with a UV transmissive or over-layer 1060 that forms an exposed exterior device-facing three-dimensional surface. The UV transmissive layer 1060 may be textured or include a finishing layer that does not impede the UV energy transmission. The holder may include a UV reflective substrate layer 1062. The holder provides a UV transmission system that directs UV light throughout the holder to reliably disinfect the exposed surfaces of the mobile device in each slot 1022. A UV light source may be positioned internally within the cabinet and oriented such that the UV light shines advantageously toward the UV transmissive material device holder in such a way that the UV light transmits through the holder to the device-facing surfaces of each slot. If a reflective layer is provided, it resists penetration of the UV light into the substrate and reflects that UV light back into the UV transmissive over-layer where it can contribute to UV treatment of the portable electrical devices in each slot 1022. The UV transmissive over-layer may be configured to provide generally uniform escape of UV light and therefore provide generally uniform treatment of the surfaces provided for each slot. For example, the thickness of the over-layer may diminish away from the UV light source and/or the over-layer may be textured to provide controlled escape of UV light.

FIG. 11 illustrates a perspective view of UV disinfection charging cabinet 1000. The current embodiment of the cabinet provides an open UV disinfection and charging station with devices 1001 stored in slots 1022 in a rack configuration. The cabinet includes a user interface 1012 with charge and disinfection indicators, a motion detector 1010 for detecting presence of a human being in the immediate vicinity of the cabinet 1000. Devices 1001 can be slid into the slots 1022 adjacent to the UV transmissive support structure 1020 and specifically the UV transmissive layer 1060. Once inserted, the power connector of each device 1001 can be connected via cord to a USB port 1018 as depicted in FIG. 11. Alternatively, the cabinet may include wireless power circuitry for inductively coupling power from one or more transmit coils 1016 to one or more inductive coils in the device 1001 or accompanying case.

Although the embodiments disclosed in FIGS. 6-11 refer to UV disinfection chargers that have the capability to charge the devices being disinfected, some alternative embodiments may not provide charging capability and instead a UV disinfection rack may be provided in accordance with the present invention that includes a UV transmissive support surface for directing UV energy along a UV transmission path to disinfect the device, case, and/or surfaces within the rack, without the capability to provide power to the device.

Operation of the controller, charging circuitry, and UV disinfection circuitry in the UV disinfection charger can be implemented in a variety of ways. The charge controller can implement a variety of known methods for regulating electric current from a battery or electric current from the power supply 1034. The charge controller 1030 can be programmed to prevent overcharging and protect against overvoltage. The charge controller can also be programmed to supply power according to a variety of different protocols and according to a variety of different parameters. For example, the charge controller 1030 can efficiently and intelligently divide power supply among the source driver 1032, and device 2001 through the power connector 1018. The controllers 410, 622, 1030 can also act as a UV disinfection control system that energizes a UV-C power source that enables UV-C intensity control and contact time control. The UV-C source may be essentially any UV-C source capable of generating UV-C light at the desired intensities. For example, the UV-C source may be a cold cathode lamp, a low pressure mercury lamp or UV-C light emitting diodes. The control system of each of the embodiments can be coupled to a sensor system that provides the system with various sensor inputs, such as passive infrared ("PIR") sensors, motion sensors, capacitive touch sensors, accelerometer and temperature sensors, and may provide an interface for an RFID reader. The data collected by these sensors may assist in controlling operation of the system and in collecting data that may be relevant to tracking disinfection activity. The motion and presence detection can trigger UV source activation, to interrupt disinfection cycles and to provide valuable data in making dynamic adjustments to the UV parameters, such as cycle time and source intensity. Although the PIR solution for heat and motion may be popular today, capacitive touch sensing is another solution. The controllers 410, 622, 1030 of the described embodiments can also monitor the current and voltage within preset ranges for proper operation and lamp diagnostics. Sources can be open, shorted, impedance can change causing different operating voltages that the controller can identify and send respond to. The UV-C power source can also monitor the current and voltage to the UV source and feed that information back to the controller. The controller 36 may also include volatile and and/or non-volatile storage memory. For example, the controller may include flash memory. The operation of the controller and related UV disinfection circuitry can be implemented or adapted partially or in full as described in U.S. provisional patent application 62/650,340, entitled Disinfection Behavior Tracking and Ranking, filed on Mar. 30, 2018 to Baarman, which is hereby incorporated by reference in its entirety.

The application programming interface of any of the controllers in the described or other embodiments can track charging cycles for each device, number of cleaning cycles, and usage including typical use times. This data can be stored locally or remotely on a server, for example on the Internet. The data can be used to track the disinfection process and functionality for maintenance and ongoing working status.

The UV disinfection charger can utilize a sensor system in order to detect presence of human activity and automatically interrupt UV source activation. Further, by providing an open interface along with an easily understood indicator system, devices can be retrieved and replaced efficiently and easily. Conventional UV disinfection systems often require devices to be locked in a cabinet so that users are not exposed to the higher dosing of UV energy that is utilized to ensure devices are fully disinfected. However, these conventional systems have a hidden cost because users may refrain or be deterred from using the cabinet because of the perceived or actual time associated with turning off any ongoing disinfection process, unlocking the cabinet door, opening the cabinet door, inserting/retrieving the device, closing the cabinet door, locking the cabinet door, and restarting the disinfection.

The UV disinfection charger depicted in FIG. 11 addresses this issue by providing an open architecture that allows a device to be grabbed without having to unlock or open a door. In addition, sensors and control interlocks can detect human activity and automatically change operation of the system. For example, a motion detection system, such as a passive infrared sensor, can reliably identify whether there is human activity in the vicinity of the rack and can automatically change operation of the system to ensure any ongoing disinfection is not harmful to the user. For example, the system can automatically turn off the UV sources when human presence is detected. Or, alternatively, the system can change operation of the UV source intensity. In addition, the depicted UV disinfecting charger 1000 utilizes low dose UV-C source, which is safer for users' eyes and contact. Further, the UV-C source utilizes a lower minimal dose rate, which is compensated with extended cycle times to provide that same effect as overdosing but with better results in surface breakdown. Providing the lower doses does not break down the plastics in the same way that higher dosages do. Further, the provided user interface 1012 allows a user to identify at a glance if a device is charged and disinfected, which reduces the amount of time spent in the vicinity of the charging rack. The UV transmissive support structure and/or UV transmissive cases used in conjunction with the UV disinfecting charging rack also assist in ensuring that in embodiments where the UV source is allowed to operate at some capacity with a user present, that the UV light is directed toward the device. In addition, in embodiments where wireless power charging is provided, the user does not spend time connecting/disconnecting cords with the UV disinfecting charging rack and therefore the time spent with human presence at the rack is reduced, which ultimately increases charging and disinfection rates. Additionally, these cordless solutions for UV transmissive cases and mobile devices allow elimination of areas for bacterial and pathogens to grow.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

The embodiments of the invention in which an exclusive property or privilege is claimed are defined as follows:

1. A UV disinfecting charger for disinfecting and charging a portable electrical device supported by the UV disinfecting charger, the UV disinfecting charger comprising:
    a UV source;
    a UV transmissive support surface disposed adjacent the UV source;
    a disinfection control system that operates the UV source to generate UV light at the UV transmissive support surface such that the UV transmissive supporting surface encourages the UV light along a UV light path that travels 360 degrees about the portable electrical device providing 3D disinfection of the portable electrical device; and
    a charging control system that provides power to the portable electrical device.

2. The UV disinfecting charger of claim 1 wherein the UV transmissive supporting surface assist the UV light to reach difficult areas to disinfect.

3. The UV disinfecting charger of claim 1 including a sensor system, wherein the disinfection control system is configured to halt disinfection within 1 ms of detection of a user in proximity to the UV disinfecting charger.

4. The UV disinfecting charger of claim 1 wherein the UV source includes a first UV light source and a second UV light source, wherein the first UV light source is located below the UV transmissive support surface and wherein said second UV light source is located above the portable electrical device.

5. The UV disinfecting charger of claim 1 including a user interface that indicates charging status and disinfection status of the portable electrical device.

6. The UV disinfecting charger of claim 1 wherein the disinfection control system and charging control system track information relating to portable electrical device usage, charging, and disinfection.

7. A UV disinfecting charging cabinet for disinfecting and charging a plurality of portable electrical devices supported by the UV disinfecting charging cabinet, the UV disinfecting charging cabinet:
    a plurality of UV sources;
    a UV transmissive support holder disposed adjacent the plurality of UV sources, the UV transmissive support holder including a plurality of slots for receiving a plurality of portable electrical devices, wherein each of the slots are lined with UV transmissive material;
    a disinfection control system that operates the plurality of UV sources to generate UV light at the UV transmissive support holder such that the UV transmissive support holder encourages the UV light along a UV light path along the UV transmissive material lining the plurality of slots such that UV light travels 360 degrees about each of the plurality of portable electrical devices held in the plurality of slots providing 3D disinfection of each of the portable electrical devices; and
    a charging control system that provides power to each of the portable electrical devices.

8. The UV disinfecting charging cabinet of claim 7 wherein the UV transmissive support holder directs UV light to reach difficult areas to disinfect.

9. The UV disinfecting charging cabinet of claim 7 including a motion sensor, wherein the disinfection control system is configured to halt disinfection within 1 ms of detection of a user in proximity to the UV disinfecting charging cabinet.

10. The UV disinfecting charging cabinet of claim 7 wherein each of the plurality of UV sources are disposed adjacent at least one of the plurality of slots.

11. The UV disinfecting charging cabinet of claim 7 including a user interface that indicates charging status and disinfection status of each of the plurality of portable electrical devices.

12. The UV disinfecting charging cabinet of claim 7 wherein the disinfection control system and charging control system track information relating to portable electrical device usage, charging, and disinfection.

13. A UV disinfecting charger for disinfecting and charging a portable electrical device supported by the UV disinfecting charger, the UV disinfecting charger comprising:
a UV source;
a support surface disposed adjacent the UV source, the support surface having a UV transmissive portion;
a disinfection control system that operates the UV source to generate and direct UV energy toward the support surface such that the UV transmissive portion of the support surface encourages the UV energy along a UV energy path about the portable electrical device providing disinfection of external surfaces of the portable electrical device; and
a charging control system that supplies power to the portable electrical device.

14. The UV disinfecting charger of claim 13 wherein the UV transmissive portion assists in directing the UV energy toward areas of the portable electrical device hidden from view while placed the portable electrical device is positioned on the support surface.

15. The UV disinfecting charger of claim 13 including a sensor system, wherein the disinfection control system is configured to halt disinfection in response to detection of a user in proximity to the UV disinfecting charger.

16. The UV disinfecting charger of claim 13 wherein the UV source includes a first UV energy source and a second UV energy source, wherein the first UV energy source is located below the support surface and wherein said second UV energy source is located above the portable electrical device.

17. The UV disinfecting charger of claim 13 including a user interface that indicates charging status and disinfection status of the portable electrical device.

18. The UV disinfecting charger of claim 13 wherein the disinfection control system and charging control system track information relating to portable electrical device usage, charging, and disinfection.

19. The UV disinfecting charger of claim 13 including a sensor system configured to monitor one or more of capacitance and motion, and in response shut off or reconfigure the UV disinfection charger.

20. The UV disinfecting charger of claim 13 wherein the UV source is a low dose UV source.

* * * * *